(12) United States Patent
Tiekemeier et al.

(10) Patent No.: US 9,462,806 B2
(45) Date of Patent: Oct. 11, 2016

(54) USE OF PEROXYCARBOXYLIC ACIDS FOR COLD ASEPTIC FILLING

(75) Inventors: Julia Tiekemeier, Duesseldorf (DE); Petra Vogt, St. Paul, MN (US); Junzhong Li, Eagan, MN (US); David McSherry, St. Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 223 days.

(21) Appl. No.: 14/394,992

(22) PCT Filed: Apr. 16, 2012

(86) PCT No.: PCT/IB2012/051891
§ 371 (c)(1),
(2), (4) Date: Jan. 19, 2015

(87) PCT Pub. No.: WO2013/156813
PCT Pub. Date: Oct. 24, 2013

(65) Prior Publication Data
US 2015/0164071 A1   Jun. 18, 2015

(51) Int. Cl.
| | | |
|---|---|---|
| A01N 41/04 | (2006.01) |
| A01N 59/00 | (2006.01) |
| A01N 37/16 | (2006.01) |
| C11D 3/48 | (2006.01) |
| C11D 3/39 | (2006.01) |
| C11D 7/26 | (2006.01) |
| C11D 11/00 | (2006.01) |
| A01N 37/02 | (2006.01) |

(52) U.S. Cl.
CPC .............. *A01N 41/04* (2013.01); *A01N 37/02* (2013.01); *A01N 37/16* (2013.01); *A01N 59/00* (2013.01); *C11D 3/3945* (2013.01); *C11D 3/48* (2013.01); *C11D 7/265* (2013.01); *C11D 11/0041* (2013.01)

(58) Field of Classification Search
USPC ....................................................... 424/405
See application file for complete search history.

(56) References Cited

U.S. PATENT DOCUMENTS

| | | | |
|---|---|---|---|
| 5,314,687 A | 5/1994 | Oakes et al. |
| 6,262,013 B1 | 7/2001 | Smith et al. |
| 6,803,057 B2 | 10/2004 | Ramirez et al. |
| 2002/0192297 A1 | 12/2002 | Ramirez et al. |
| 2010/0048730 A1 | 2/2010 | Li et al. |

FOREIGN PATENT DOCUMENTS

| | | |
|---|---|---|
| WO | WO2009/118714 | 10/2009 |
| WO | 2013009754 A2 | 1/2013 |

*Primary Examiner* — Walter Webb
(74) *Attorney, Agent, or Firm* — Amy J. Hoffman

(57) ABSTRACT

The present invention relates to compositions, methods of making and their use as cleaning composition and/or antimicrobial agent, for example in the field of cold aseptic filling (CAF), that are effective at lower concentration, having improved wetting and rinsing properties, wherein the liquid composition comprises a mixture of:
a) a C6 to C22 sulfoperoxycarboxylic acid,
b) a $C_1$ to $C_4$ percarboxylic acid,
c) a $C_5$ to $C_{10}$ percarboxylic acid,
d) a peroxide agent,
e) a liquid; wherein
the composition comprises free sulfocarboxylic acid, free $C_1$ to $C_4$ carboxylic acid and free $C_5$ to $C_{10}$ carboxylic acid, wherein the weight ratio of C6 to C22 sulfocarboxylic acid to C6 to C22 sulfoperoxycarboxylic acid is about 0.1:1 to about 25:1.

19 Claims, No Drawings

USE OF PEROXYCARBOXYLIC ACIDS FOR COLD ASEPTIC FILLING

FIELD OF THE INVENTION

The present invention relates to peroxycarboxylic compositions, methods of making and their use as cleaning composition and/or antimicrobial agent, for example in the field of cold aseptic filling (CAF), that are effective at lower concentration, having improved wetting and rinsing properties.

BACKGROUND

Peroxycarboxylic acids are known for use as antimicrobial agents. However, conventional peroxycarboxylic acids have inherent disadvantages of limited storage stability, and water solubility. Peroxycarboxylic acids compositions are not effective if low concentrated and/or used at lower temperatures. Further, most peroxycarboxylic acids have an unpleasant odor.

Clean in place (CIP) cleaning techniques are a specific cleaning and disinfection regimen adapted for removing soils from the internal components of tanks, lines, pumps and other process equipment used for processing typically liquid product streams such as beverages, milk, juices, etc. Clean in place cleaning involves passing cleaning solutions through the system without dismantling any system components. The minimum clean-in-place technique involves passing the cleaning solution through the equipment and then resuming normal processing.

Clean out of place systems (COP) cleaning techniques are a specific cleaning and disinfection regimen adapted for removing soils from interior and exterior surfaces of a wide variety of parts, such as ceramic surfaces, metal surfaces, walls in, wash tanks, soaking vessels, mop buckets, holding tanks, scrub sinks, vehicle parts washers, non-continuous batch washers and systems, and the like.

Cold aseptic filling (CAF) involves bottling a product at ambient or even lower temperatures. Aseptic filling is recommended for beverages such as fruit juices, tea beverages, sports drinks, vegetable juices, milk-based mixed drinks, ultra-heat treated (UHT) milk, near-water drinks and flavored waters. It can be used for both still and carbonated beverages. In the 'wet' aseptic process, containers are sterilized using peracetic acid ($C_2H_4O_3$) and steam. However, peracetic acid has an unpleasant odor. Further, pure peracetic acid ($C_2H_4O_3$) requires a relatively high use concentration. Moreover, the spreading and penetrating properties of peracetic acid are insufficient due to its high surface tension. Thus, peracetic acid needs more intensive rinsing, in particular when applied on plastic surfaces due to its hydrophobic properties, which does not make it very suitable for standard, high speed filling lines.

In some cases, instead of the commonly used wet sterilization process using peracetic acid, a dry sterilization process using $H_2O_2$ (hydrogen peroxide) is recommended.

Cold-aseptic filling is now a widely used process that is consistently being adapted to new demands.

Compositions used in clean in place, in clean out of place processes, and in particular in the field of cold-aseptic filling, have the drawback that the soaking time on an upright tiled wall is short due to a good flow rate of the liquid cleaning composition.

Also, peroxide containing compositions used in clean in place, in clean out of place processes, and in particular in the field of cold-aseptic filling are not storage stable, i.e. the compositions have a tendency of phase separation, which has the disadvantage of a dramatically decreased antimicrobial effect.

Further, compositions used in COP, CIP as well as in CAF processes have a tendency of leaving residues on the treated surface, which requires an increased number of rinsing cycles and increased water and energy consumption.

Thus there is a need for effective cleaning techniques that also reduce energy requirements, improve operations, save time and increase operational safety.

SUMMARY OF THE INVENTION

In some embodiments, the present invention relates to sulfoperoxycarboxylic acids containing compositions having improved wetting and rinsing properties, and methods for making them.

In some embodiments, the present invention relates to storage stable sulfoperoxycarboxylic acids containing compositions, and methods for making them.

In some embodiments, the present invention relates to low or no-foaming sulfoperoxycarboxylic acids containing compositions.

In some embodiments, the present invention relates to storage stable sulfoperoxycarboxylic acids containing compositions that are phase stable, having low or no-odor, are effective at lower temperatures, and are water soluble.

In some embodiments, the present invention provides methods for using the compositions of the present invention as cleaning and/or antimicrobial agents.

In some embodiments, the present invention provides methods for using the compositions of the present invention in the field of cold aseptic filling (CAF).

In some embodiments, the present invention provides methods for using the compositions for clean in place (CIP) cleaning processes, for example for cleaning tanks, lines, pumps and other process equipment used for processing typically liquid product streams of beverages, in particular for cleaning milking machines.

In some embodiments, the present invention provides methods for using the compositions for clean out of place (COP) cleaning processes, for example from interior and exterior surfaces of a wide variety of parts, such as ceramic surfaces, metal surfaces, walls in, wash tanks, soaking vessels, mop buckets, holding tanks, scrub sinks, vehicle parts washers, non-continuous batch washers and systems, and the like.

In some embodiments, the compositions are suitable for use as low temperature cleaning, bleaches and/or antimicrobial agents, preferably in the field of CAF at temperatures in between 40° C. to 60° C.

In some embodiments, the compositions of the present invention are suitable for use as pH optimized peroxygen bleaches and/or antimicrobial agent in detergents.

In some embodiments, the compositions of the present invention are suitable for use as cleaning composition that minimizes energy having excellent disinfection properties, preferably in the food, beverage and/or meat processing industry.

DETAILED DESCRIPTION

The present invention relates to a liquid composition comprising a mixture of:
a) a C6 to C22 sulfoperoxycarboxylic acid,
b) a $C_1$ to $C_4$ percarboxylic acid,
c) a $C_5$ to $C_{10}$ percarboxylic acid, d) a peroxide agent,
e) a liquid; wherein the composition comprises free sulfocarboxylic acid, free $C_1$ to $C_4$ carboxylic acid and free $C_5$ to $C_{10}$ carboxylic acid, wherein the weight ratio of C6 to C22 sulfocarboxylic acid to C6 to C22 sulfoperoxycarboxylic acid is about 0.1:1 to 25:1.

According to one embodiment the liquid composition comprises a mixture of:
a) a C6 to C22 sulfoperoxycarboxylic acid,
b) a $C_1$ to $C_4$ percarboxylic acid,
c) a $C_5$ to $C_{10}$ percarboxylic acid,
d) a peroxide agent,
e) a hydrotrope,
f) a liquid; wherein the composition comprises free sulfocarboxylic acid, free $C_1$ to $C_4$ carboxylic acid and free $C_5$ to $C_{10}$ carboxylic acid, wherein the weight ratio of C6 to C22 sulfocarboxylic acid to C6 to C22 sulfoperoxycarboxylic acid is about 0.1:1 to 25:1.

According to another embodiment the liquid composition comprises a mixture of:
a) a C6 to C22 sulfoperoxycarboxylic acid,
b) a $C_1$ to $C_4$ percarboxylic acid,
c) a $C_5$ to $C_{10}$ percarboxylic acid,
d) a peroxide agent,
e) a hydrotrope,
f) a chelant, preferably dipicolinic acid and/or a phosphonic acid
g) a liquid; wherein the composition comprises free sulfocarboxylic acid, free $C_1$ to $C_4$ carboxylic acid and free $C_5$ to $C_{10}$ carboxylic acid, wherein the weight ratio of C6 to C22 sulfocarboxylic acid to C6 to C22 sulfoperoxycarboxylic acid is about 0.1:1 to 25:1.

In some embodiments the weight ratio of C6 to C22 sulfocarboxylic acid to C6 to C22 sulfoperoxycarboxylic acid is about 0.1:1 to about 25:1, especially about 0.5:1 to about 23:1, in particular about 1:1 to about 22:1, preferably about 5:1 to about 20:1, further preferred about 4:1 to about 15:1 and also preferred about 3:1 to about 10:1.

The peroxide agent d) is different to the percarboxylic acids a), b) and c). Preferably, the peroxide agent d) is not a percarboxylic acid.

Generally, the use of $C_1$ to $C_4$ percarboxylic acid, such as peracetic acid, as the sole percarboxylic acid requires a high concentration of peracetic acid. Further, peracetic acid has poor wetting performance. The spreading and penetrating properties of peracetic acid are insufficient due to its high surface tension, thus peracetic acid needs more intensive rinsing, in particular when applied on plastic surfaces due to its hydrophobic properties, which does not make it very suitable for standard, high speed filling lines. Surprisingly, it has been found that the surfactant properties of C6 to C22 sulfocarboxylic acid (SOA) and C6 to C22 sulfopercarboxylic acid (PSOA) promotes the rinsability thereof.

Generally, the use of $C_5$ to $C_{10}$ percarboxylic acid, such as peroctanoic acid, as the sole percarboxylic acid, is not an effective cleaning composition due to its unpleasant odor and poor rinsing performance, too.

In some embodiments the composition can be a concentrated liquid composition or a diluted liquid composition, also referred as use solution. The use solution can be obtained from a concentrated solution by thinning the concentrated solution with a solvent, preferably water. A concentrated solution has advantages in transporting and storing. The concentrated liquid, storage stable, concentrated composition can be further diluted, for example prior to use, by admixing a solvent, preferably water.

In some embodiments of the concentrated liquid composition the concentration of the $C_1$ to $C_4$ percarboxylic acid is about ≥2.5 wt.-% to about ≤16.5 wt.-% and the concentration of the $C_5$ to $C_{10}$ percarboxylic acid is about ≥0.01 wt.-% to about ≤8 wt.-%, based on the total weight of the concentrated liquid composition.

In some embodiments of the concentrated liquid composition comprises a mixture of:
a) about ≥0.01 wt.-% to about ≤25 wt.-%, preferably about ≥0.05 wt.-% to about ≤15 wt.-%, further preferred about ≥0.1 wt.-% to about ≤10 wt.-%, additionally preferred ≥0.2 wt.-% to about ≤1 wt.-%, and also preferred about ≥0.3 wt.-% to about ≤0.5 wt.-%, of at least one C6 to C22 sulfocarboxylic acid, preferably sulphonated oleic acid;

b) about ≥0.001 wt.-% to about ≤2 wt.-%, preferably about ≥0.01 wt.-% to about ≤1.5 wt.-%, further preferred ≥0.03 wt.-% to about ≤1 wt.-%, and also preferred ≥0.05 wt.-% to about ≤0.1 wt.-%, of a C6 to C22 sulfoperoxycarboxylic acid, preferably sulfonated peroxyoleic acid;

c) about ≥10 wt.-% to about ≤50 wt.-%, preferably about ≥15 wt.-% to about ≤40 wt.-%, further preferred ≥18 wt.-% to about ≤30 wt.-%, and also preferred ≥20 wt.-% to about ≤27 wt.-%, of a C1 to C4 carboxylic acid, preferably acetic acid;

d) about ≥2.5 wt.-% to about ≤16.5 wt.-%, preferably about ≥5 wt.-% to about ≤16 wt.-%, further preferred ≥6 wt.-% to about ≤15 wt.-%, and also preferred ≥7 wt.-% to about ≤13.5 wt.-%, of a $C_1$ to $C_4$ peroxycarboxylic acid, preferably peracetic acid;

e) about ≥0 wt.-% to about ≤10 wt.-%, preferably about ≥0.01 wt.-% to about ≤5 wt.-%, further preferred ≥0.1 wt.-% to about ≤2 wt.-%, in addition preferred ≥0.2 wt.-% to about ≤1 wt.-%, and also preferred ≥0.3 wt.-% to about ≤0.7 wt.-%, of a $C_5$ to $C_{10}$ carboxylic acid, preferably octanoic acid;

f) about ≥0 wt.-% to about ≤8 wt.-%, preferably about ≥0.001 wt.-% to about ≤6 wt.-%, further preferred ≥0.01 wt.-% to about ≤2 wt.-%, in addition preferred ≥0.1 wt.-% to about ≤1 wt.-%, and also preferred ≥0.2 wt.-% to about ≤0.5 wt.-%, of a $C_5$ to $C_{10}$ percarboxylic acid, preferably peroxyoctanoic acid;

g) about ≥5 wt.-% to about ≤30 wt.-%, preferably about ≥7 wt.-% to about ≤25 wt.-%, further preferred ≥12 wt.-% to about ≤20 wt.-%, and also preferred ≥16 wt.-% to about ≤18 wt.-%, of at least one peroxide agent, preferably hydrogen peroxide, h) about ≥0 wt.-% to about ≤20 wt.-%, preferably about ≥5 wt.-% to about ≤18 wt.-%, further preferred about ≥8 wt.-% to about ≤15 wt.-%, and in addition preferred about ≥10 wt.-% to about ≤12 wt.-%, of a hydrotrope, preferably selected from the group comprising of a xylene sulfonate, toluene sulfonate, cumene sulfonate, n-octane sulfonate, and/or acids thereof and more preferred is cumene sulfonate;

i) about ≥0 wt.-% to about ≤10 wt.-%, preferably about ≥0.1 wt.-% to about ≤5 wt.-%, further preferred ≥0.3 wt.-% to about ≤2.5 wt.-%, and also preferred ≥0.5 wt.-% to about ≤1 wt.-%, of a chelant, preferably dipicolinic acid and/or a phosphonic acid and also preferred a 1-hydroxyethane-(1,1-diphosphonic acid) (HEDP);

j) a liquid, preferably water; wherein the components are selected such that the total weight amount of all components of the concentrated liquid composition is 100 wt.-%.

In some embodiments the concentrated liquid composition is obtained by mixing:
i) about ≥10 wt.-% to about ≤30 wt.-% of at least one peroxide agent;
ii) carboxylic acids of:
about ≥0.01 wt.-% to about ≤25 wt.-% of at least one C6 to C22 sulfocarboxylic acid,
about ≥10 wt.-% to about ≤60 of at least one C1 to C4 carboxylic acid, about ≥0.01 wt.-% to about ≤10%, preferably about ≥0.1 wt.-% to about ≤2%, in addition preferred ≥0.3 wt.-% to about ≤0.7 wt.-%, of at least one $C_5$ to $C_{10}$ carboxylic acid;
iii) about ≥0 wt.-% to about ≤20 wt.-%, preferably about ≥5 wt.-% to about ≤18 wt.-%, further preferred about ≥8 wt.-% to about ≤15 wt.-%, and in addition preferred about ≥10 wt.-% to about ≤12 wt.-%, of at least one hydrotrope, preferably selected from the group comprising of a xylene sulfonate, toluene sulfonate, cumene sulfonate, n-octane sulfonate, and/or acids thereof and more preferred is cumene sulfonate,
iv) about ≥0 wt.-% to about ≤10 wt.-%, preferably about ≥0.1 wt.-% to about ≤5 wt.-%, further preferred ≥0.3 wt.-% to about ≤2.5 wt.-%, and also preferred ≥0.5 wt.-% to about ≤1 wt.-%, of a chelant, preferably dipicolinic acid and/or a phosphonic acid and also preferred a 1-hydroxyethane-(1,1-diphosphonic acid) (HEDP);
v) solvent, preferably water, wherein the components are selected such that the total weight amount of all components of the concentrated liquid composition is 100 wt.-%.

The peroxide agent i) is different to or not a percarboxylic acid.

In some other embodiments the concentrated liquid composition may comprise in addition at least one acidulant, also referred to as "additional acidulant", preferably sulfuric acid, in an amount of about ≥0 wt.-% to about ≤20 wt.-%, preferably about ≥5 wt.-% to about ≤15 wt.-%, and further preferred about ≥10 wt.-% to about ≤12 wt.-%. The acidulant has an improved solubilizing effect with respect to the carboxylic acids of the concentrated liquid composition.

In some embodiments the concentrated liquid composition as well as the use composition of the invention does not contain an additional acidulant. Thus, the concentrated liquid composition as well as the use composition of the invention is free of an additional acidulant. However, it has surprisingly been found that hydrotropes, for example cumolsulfonate, linear alkylbenzene sulphonates (LAS), xylene sulfonate, and/or cumolsulfonate, preferably cumolsulfonate, have a good solubilizing effect too.

It should be understood that the concentrated liquid composition of the invention can be free of at least one additive, preferably all additives, selected from the group of dye, color transfer inhibitor, anti-redeposition agents, optical brighteners, builder, oil and water repellant agents, color fastness agents, starch/sizing agents, fabric softening agents, fungicides, UV absorbers, thickeners, fragrances and/or mixtures thereof.

Preferably, the concentrated liquid composition of the invention can be free of an additional bleaching agent, except peroxide agent.

In some preferred embodiment the peroxide components of the concentrated liquid composition are preferably a mixture of peracetic acid, sulfoperoxycarboxylic acid, peroctanoic acid, and $H_2O_2$.

The concentrated liquid compositions of the present invention are low-odor, low foaming, water soluble and storage stable. The composition has improved rinsing properties. Further, the composition is effective at lower concentration. In addition, the composition may be effective at lower temperatures. Furthermore, the composition has improved disinfection properties.

The compositions of the present invention have many uses including, but not limited to disinfection and/or cleaning, in particular in the field of cold aseptic filling (CAF), for example in the field of cold aseptic filling (CAF) in the beverage and dairy industry. In some embodiments the composition can be used for reduction of bacterial and/or bacterial spores.

So that the invention maybe more readily understood, certain terms are first defined.

As used herein, "weight percent", "wt-%", "percent by weight", "% by weight", and variations thereof refer to a composition, component, substance or agent as the weight of that composition, component, substance or agent of the concentrated liquid composition as well as use composition divided by the total weight of the concentrated liquid composition or use composition and multiplied by 100. It is understood that the total weight percent amount of all components, substances or agents of the concentrated liquid composition as well as use composition are selected such that it does not exceed 100 wt.-%.

It is understood that, as used here, "percent", "%", and the like are intended to be synonymous with "weight percent", "wt-%", etc.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

It should be noted that, as used in this specification and the appended claims, the singular forms "a", "an", and "the" include plural referents unless the content clearly dictates otherwise. Thus, for example, reference to a concentrated liquid composition as well as reference to the use composition containing "a compound" includes a composition having two or more compounds unless the content clearly dictates otherwise.

It should also be noted that the term "or" is generally employed in its sense including, "and/or" unless the content clearly dictates otherwise.

As used herein, the phrases "objectionable odor", "offensive odor", or "malodor", refer to a sharp, pungent, or acrid odor or atmospheric environment from which a typical person withdraws if they are able to. Hedonic tone provides a measure of the degree to which an odor is pleasant or unpleasant.

An "objectionable odor", "offensive odor", or "malodor" has an hedonic tone rating it as unpleasant as or more unpleasant than a solution of 5 wt-% acetic acid, propionic acid, butyric acid, or mixtures thereof.

As used herein, the term "microorganism" refers to any non-cellular or unicellular (including colonial) organism.

Microorganisms include all prokaryotes. Microorganisms include bacteria (including cyanobacteria), spores, lichens, fungi, protozoa, virinos, viroids, viruses, phages, and some algae.

As used herein, the term "microbe" is synonymous with microorganism.

As used herein, the phrase "food product" includes any food substance that might require treatment with an antimicrobial agent or composition and that is edible with or without further preparation. Food products include beverages, e.g. non-alcoholic beverages, e.g. milk, fruit based beverages, alcoholic beverages, e.g. beer, meat, e.g. red meat and pork, seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof.

As used herein, the term "cleaning" refers to a method or process used to facilitate or aid in soil removal, microbial population reduction, and any combination thereof.

The methods, and compositions of the present invention can include, consist essentially of, or consist of the steps, and ingredients of the present invention as well as other ingredients described herein.

As used herein, "consisting essentially of" means that the methods, and compositions may include additional steps, or ingredients, but only if the additional steps, or ingredients do not materially alter the basic and novel characteristics of the claimed methods, and compositions.

The term "produce" refers to food products such as fruits and vegetables and plants or plant-derived materials that are typically sold uncooked and, often, unpackaged, and that can sometimes be eaten raw.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the term "surface" refers to a surface of a tool, a machine, equipment, a structure, a building, or the like that is employed as part of a food processing, preparation, or storage activity. Examples of food processing surfaces include surfaces of food processing or preparation equipment, e.g., slicing, canning, or transport equipment, including flumes, of food processing wares, e.g., utensils, dishware, wash ware, and bar glasses), and of floors, walls, or fixtures of structures in which food processing occurs. Food processing surfaces are found and employed in milking machines, food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

As used herein, the term "ware" refers to items such as eating and cooking utensils, dishes, and other hard surfaces such as showers, sinks, toilets, bathtubs, countertops, windows, mirrors, transportation vehicles, and floors.

As used herein, the term "ware washing" refers to washing, cleaning, or rinsing ware.

Ware also refers to items made of plastic. Types of plastics that can be cleaned with the compositions according to the invention include but are not limited to, those that include polycarbonate polymers (PC), acrylonitrile-butadiene-styrene polymers (ABS), and polysulfone polymers (PS). Another exemplary plastic that can be cleaned using the compounds and compositions of the invention include polyethylene terephthalate (PET).

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process waters or transport waters. Food process waters or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like.

Waters also include domestic and recreational waters such as pools, spas, recreational flumes and water slides, fountains, and the like. As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry.

Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, "agricultural" or "veterinary" objects or surfaces include animal milking machines, animal feeds, animal watering stations and enclosures, animal quarters, animal veterinarian clinics (e.g. surgical or treatment areas), animal surgical areas, and the like.

In some embodiments, the present invention relates to compositions and methods for removing soils from surfaces to be cleaned. Surfaces to be cleaned are hard and/or soft surfaces. In some embodiments, the composition of the invention is applied in a clean in place process (CIP) and/or in a clean out of place process (COP). In other embodiments, the compositions of the invention may be manually applied to the surface to be cleaned. In particular the concentrated liquid compositions of the invention as well as the use composition o the invention can be applied in cold aseptic filling (CAF) processes, for example in the beverage and food processing industry, such as milk processing industry, for disinfection purposes.

In some embodiments, the methods and compositions of the present invention may be applied to equipment generally cleaned using cold aseptic filling cleaning procedures (CAF).

Exemplary industries in which the methods and concentrated liquid compositions of the present invention can be used include, but are not limited to: the food and beverage industry, e.g., the milk machine, milk processing industry, meat processing industry; dairy, cheese, sugar, and brewery industries, e.g. milk; oil processing industry; industrial agriculture and ethanol processing; and the pharmaceutical manufacturing industry.

As used herein, the term "sanitizer" refers to an agent that reduces the number of bacterial contaminants to safe levels as judged by public health requirements.

In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 252° C., against several test organisms.

As used herein, the term "disinfectant" refers to an agent that kills all vegetative cells including most recognized pathogenic microorganisms, using the procedure described in A. O. A. C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used in this invention, the term "sporicide" refers to a physical or chemical agent or process having the ability to cause greater than a 90% reduction (1-log order reduction) in the population of spores for example of Bacillus cereus or Bacillus subtilis, Bacillus athrophaeus, Chaetomium globosum and/or Paenibacillus chibensis within 10 seconds at 60° C. In certain embodiments, the sporicidal compositions of the invention provide greater than a 99% reduction (2-log order reduction), greater than a 99.9% reduction (3-log order reduction), greater than a 99.99% reduction (4-log order reduction), or greater than a 99.999% reduction (5-log order reduction) in such population within 10 seconds at 60° C. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition Larger reductions in microbial population provide greater levels of protection.

Compounds of the Invention

The present invention relates, at least in part, to C6 to C22 sulfocarboxylic acid and C6 to C22 sulfoperoxycarboxylic acid containing concentrated liquid compositions and the use thereof in a variety of disinfecting and cleaning applications.

In some embodiments of the invention the sulfocarboxylic acid and/or sulfoperoxycarboxylic acid is a C6 to C22 sulfonated carboxylic acid, preferably a C10 to C20 sulfonated carboxylic acid, also preferred a C14 to C18 sulfonated carboxylic acid.

The term "sulfocarboxylic acid" or "sulfonated carboxylic acid" are synonymous used herein.

As used herein, the term "sulfoperoxycarboxylic acid" or "sulfonated peroxycarboxylic acid" refers to the peroxycarboxylic acid obtained by oxidizing of the corresponding sulfonated carboxylic acid.

In some embodiments, compositions of the present invention can include one or more of the sulfoperoxycarboxylic acids of the present invention.

Sulfoperoxycarboxylic acid that may be suitable to use having the general Formula I:

$R_1$—CH(SO$_3$$^-$X$^+$)—$R_2$—COOOH (Formula I);

and

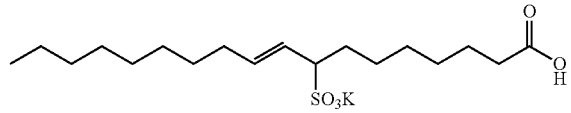

sulfocarboxylic acid that may be suitable to use having the general Formula II:

$R_1$—CH(SO$_3$$^-$X$^+$)—$R_2$—COOH (Formula II);

wherein:

$R_1$ a substituted or unsubstituted $C_m$ alkyl group, for example CH$_3$—(CH)$_7$—C═C—;

$R_2$ is hydrogen, or a substituted or unsubstituted $C_n$ alkyl group, for example —(CH$_2$)$_6$—, preferably hydrogen;

X is hydrogen (H$^+$), a cationic group, such as Na$^+$, K$^+$, or an ester-forming moiety, preferably H$^+$;

m is 1 to 10, preferably 8 to 10;

n is 1 to 10; preferably 6 to 8; and m+n is less than or equal to 18, or salts or esters thereof;

or can be represented by one of the following structures of sulfoperoxycarboxylic acids IIIa to VIIa and/or sulfocarboxylic acids IIIb to VIIb:

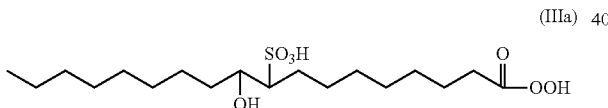
(IIIa)

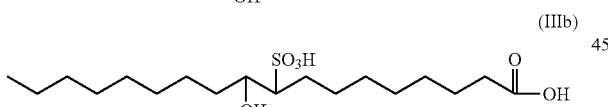
(IIIb)

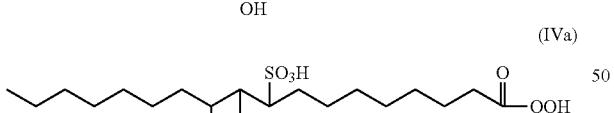
(IVa)

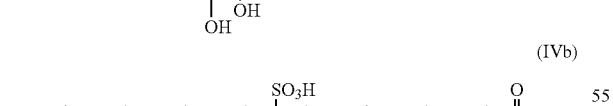
(IVb)

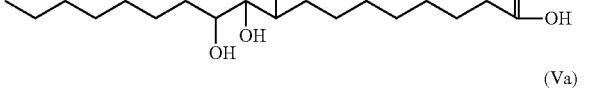
(Va)

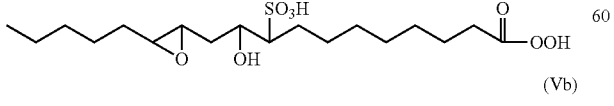
(Vb)

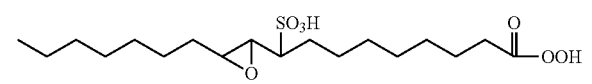
(VIa)

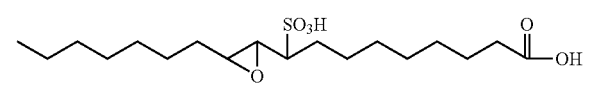
(VIb)

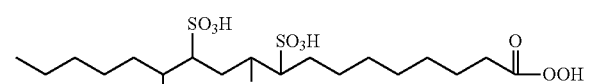
(VIIa)

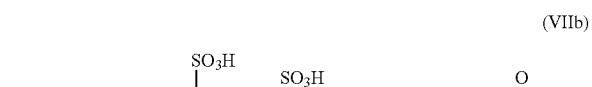
(VIIb)

According to a preferred embodiment, the composition of the present invention may comprise sulfoperoxycarboxylic acids IIIa to VIIa and/or sulfocarboxylic acids IIIb to VIIb:

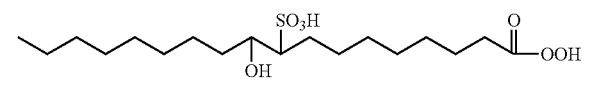
(IIIa)

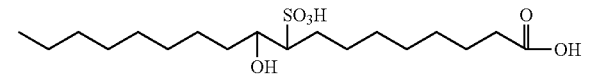
(IIIb)

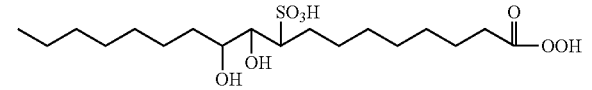
(IVa)

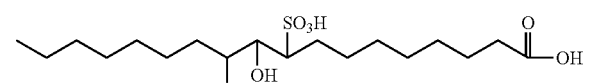
(IVb)

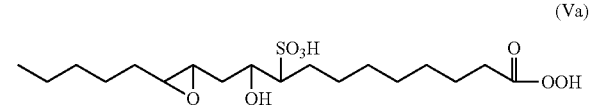
(Va)

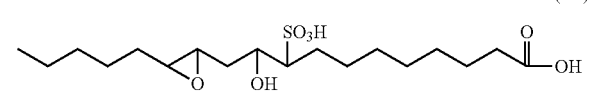
(Vb)

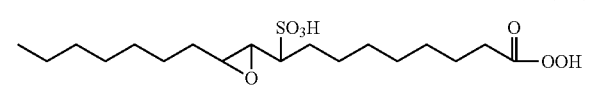
(VIa)

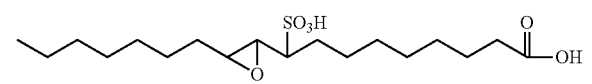
(VIb)

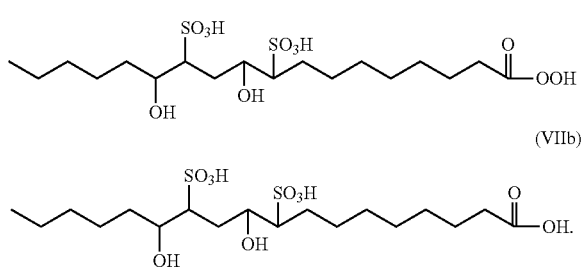

According to another preferred embodiment the sulfoperoxycarboxylic acid is $CH_3-(CH)_7-C=C-CH(SO_3^- X^+)-(CH_2)_6-COOOH$ and the sulfocarboxylic acid is $CH_3-(CH)_7-C=C-CH(SO_3^-X^+)-(CH_2)_6-COOH$.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone.

Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen.

Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Sulfoperoxycarboxylic acid obtained from oxidizing sulfocarboxylic compounds that can be suitable used according to the present invention are disclosed in WO 2009/118714 A2 and are completely disclosed by reference herewith.

In table I sulfocarboxylic acids and C6 to C22 sulfoperoxycarboxylic acids are shown that may be suitable to use for compositions of the invention:

TABLE I

| sulfocarboxylic acids | sulfoperoxycarboxylic acids |
|---|---|
| 9,10-Dihydroxy-9-sulfooctadecanoic acid | 9,10-Dihydroxy-9-sulfooctadecaneperoxoic acid |
| 10-Hydroxy-9-sulfooctadecanoic acid | 10-Hydroxy-9-sulfooctadecaneperoxoic acid |
| 9-Sulfooctadecanoic acid | 9-Sulfooctadecaneperoxoic acid |
| 11-Sulfoundecanoic acid | 11-Sulfoundecaneperoxoic acid |
| 10,11-Disulfoundecanoic acid | 10,11-Disulfoundecaneperoxoic acid |
| 8-(3-octyloxiran-2-yl)-8-sulfooctanoic acid | 8-(3-octyloxiran-2-yl)-8-sulfooctaneperoxoic acid |
| 9,10-Dihydroxy-11-sulfooctadecanoic acid | 9,10-Dihydroxy-11-sulfooctadecaneperoxoic acid |
| 8-(3-octyloxiran-2-yl)-11-sulfooctanoic acid | 8-(3-octyloxiran-2-yl)-11-sulfooctaneperoxoic acid |
| 9-Hydroxy-10-sulfooctadecanoic acid | 9-Hydroxy-10-sulfooctadecaneperoxoic acid |
| 10-Sulfooctadecanoic acid | 10-Sulfooctadecaneperoxoic acid |
| 9,10-Disulfooctadecanoic acid | 9,10-Disulfooctadecaneperoxoic acid |
| 10-Sulfoundecanoic acid | 10-Sulfoundecaneperoxoic acid |
| 9-(3-heptyloxiran-2-yl)-9-sulfononoic acid | 9-(3-heptyloxiran-2-yl)-9-sulfononaneperoxoic acid |
| 10,11-Dihydroxy-9-sulfooctadecanoic acid | 10,11-Dihydroxy-9-sulfooctadecaneperoxoic acid |
| 8,9-Dihydroxy-10-sulfooctadecanoic acid | 8,9-Dihydroxy-10-sulfooctadecaneperoxoic acid |

In some embodiments the sulfonated fatty acid of the concentrated liquid composition of the invention can be oleic acid.

In some embodiments, the amount of at least one C6 to C22 sulfoperoxycarboxylic acid, preferably sulphonated peroxyoleic acid, is about $\geq 0.001$ wt.-% to about $\leq 2$ wt.-%, preferably about $\geq 0.01$ wt.-% to about $\leq 1.5$ wt.-%, further preferred $\geq 0.03$ wt.-% to about $\leq 1$ wt.-%, and also preferred $\geq 0.05$ wt.-% to about $\leq 0.1$ wt.-%; and/or the amount of at least one C6 to C22 sulfocarboxylic acid, preferably sulphonated oleic acid, is about $\geq 0.01$ wt.-% to about $\leq 25$ wt.-%, preferably about $\geq 0.05$ wt.-% to about $\leq 15$ wt.-%, further preferred about $\geq 0.1$ wt.-% to about $\leq 10$ wt.-%, in addition preferred about $\geq 0.2$ wt.-% to about $\leq 5$ wt.-%, and also preferred about $\geq 0.3$ wt.-% to about $\leq 0.5$ wt.-%.

$C_1$ to $C_4$ Percarboxylic Acid

In some embodiments, components for use with the methods and concentrated liquid compositions of the present invention include at least one $C_1$ to $C_4$ percarboxylic acid. Examples of suitable $C_1$ to $C_4$ percarboxylic acid include, but are not limited to peroxyformic, peroxyacetic, peroxypropionic, and/or peroxybutanoic acid as well as their branched isomers, for example peroxylactic acid, peroxymaleic acid, and/or peroxyhydroxyacetic acid. However, in some embodiments peroxyacetic acid may be preferred.

In some embodiments, the amount of $C_1$ to $C_4$ percarboxylic acid of a concentrated liquid composition may be $\geq 2.5$ wt.-% to about $\leq 16.5$ wt.-%, preferably about $\geq 5$ wt.-% to about $\leq 16$ wt.-%, or about $\geq 6$ wt.-% to about $\leq 15$ wt.-% and also preferably about $\geq 7$ wt.-% to about $\leq 13.5$ wt.-%.

$C_1$ to $C_4$ Carboxylic Acid

In some embodiments, concentrated liquid compositions, suitable for use with the methods of the present invention may include at least one $C_1$ to $C_4$ carboxylic acid. Examples of suitable $C_1$ to $C_4$ carboxylic acid include, but are not limited to formic, acetic, propionic and/or butanoic acid as well as their branched isomers, for example lactic acid, maleic acid, and/or hydroxyacetic acid. However, in some embodiments acetic acid may be preferred.

In some embodiments, the amount of $C_1$ to $C_4$ carboxylic acid of a concentrated liquid composition may be $\geq 10$ wt.-% to about ≤50 wt.-%, preferably about ≥15 wt.-% to about ≤40 wt.-%, and also preferred about ≥20 wt.-% to about ≤30 wt.-%.

$C_1$ to $C_4$ Percarboxylic Acid/$C_1$ to $C_4$ Carboxylic Acid

In some embodiments, the composition comprises the $C_1$ to $C_4$ percarboxylic acid, preferably peracetic acid, in an amount of about ≥2.5 wt.-% to about ≤16.5 wt.-%, preferably about ≥5 wt.-% to about ≤16 wt.-%, further preferred about ≥6 wt.-% to about ≤15 wt.-%, and also preferred ≥7 wt.-% to about ≤13.5 wt.-%, based on the total weight of the concentrated liquid composition; and/or $C_1$ to $C_4$ carboxylic acid, preferably acetic acid, in an amount of about ≥10 wt.-% to about ≤50 wt.-%, preferably about ≥15 wt.-% to about ≤40 wt.-%, or about ≥20 wt.-% to about ≤30 wt.-%, based on the total weight of the concentrated liquid composition; and preferably a mixture of a $C_1$ to $C_4$ peracetic acid and $C_1$ to $C_4$ carboxylic acid, preferably a mixture of peracetic acid and acetic acid, in an amount of about ≥12.5 wt.-% to about ≤66.5 wt.-%, preferably about ≥20 wt.-% to about ≤55 wt.-%, or about ≥26 wt.-% to about ≤40 wt.-%, based on the total weight of the concentrated liquid composition.

$C_5$ to $C_{10}$ Percarboxylic Acid

In some embodiments, concentrated liquid compositions suitable for use with the methods of the present invention may include at least one $C_5$ to $C_{10}$ percarboxylic acid. Examples of suitable $C_5$ to $C_{10}$ percarboxylic acids include, but are not limited to peroxypentanoic acid, peroxyhexanoic acid, peroxyheptanoic acid, peroxyoctanoic acid, peroxynonanoic acid, and/or peroxydecanoic acid as well as their branched isomers, for example peroxyascorbic acid, peroxycitric acid, peroxyneopentanoic acid, peroxyneoheptanoic acid, peroxyneodecanoic acid, peroxyoxalic acid, peroxymalonic acid, peroxysuccinic acid, peroxyglutaric acid, peroxyadipic acid, peroxypimelic acid, and/or peroxysuberic acid, and mixtures thereof. However, in some embodiments peroxyoctanoic acid may be preferred.

In some embodiments the weight ratio of the $C_5$ to $C_{10}$ carboxylic acid, preferably octanoic acid, to the $C_5$ to $C_{10}$ percarboxylic acid, preferably peroctanoic acid is 1:1 to 3:1, and preferably 1.5:1 to 2.5:1.

In some other embodiments the concentrated liquid composition comprises the $C_5$ to $C_{10}$ percarboxylic acid, preferably peroctanoic acid, in an amount of about >0 wt.-% to about ≤8 wt.-%, preferably about ≥0.001 wt.-% to about ≤6 wt.-%, or about ≥0.01 wt.-% to about ≤2 wt.-%, in addition preferred ≥0.1 wt.-% to about ≤1 wt.-%, and also preferred about ≥0.2 wt.-% to about ≤0.5 wt.-%, based on the total weight of the concentrated liquid composition.

In some embodiments, the amount of $C_5$ to $C_{10}$ percarboxylic acid of a concentrated liquid composition may be >0 wt.-% to about ≤2 wt.-%, preferably about ≥0.1 wt.-% to about ≤1.2 wt.-%, about ≥0.15 wt.-% to about ≤0.8 wt.-%, and also preferred about ≥0.2 wt.-% to about ≤0.5 wt.-%, based on the total weight of the concentrated liquid composition.

$C_5$ to $C_{10}$ Carboxylic Acid

In some embodiments, the concentrated liquid compositions for use with the methods of the present invention may include at least one $C_5$ to $C_{10}$ carboxylic acid. Examples of suitable $C_5$ to $C_{10}$ carboxylic acids include, but are not limited to pentanoic acid, hexanoic acid, heptanoic acid, octanoic acid, nonanoic acid, and/or decanoic acid as well as their branched isomers, for example ascorbic acid, citric acid, neopentanoic acid, neoheptanoic acid, neodecanoic acid, oxalic acid, malonic acid, succinic acid, glutaric acid, adipic acid, pimelic acid, and/or suberic acid, and mixtures thereof. However, in some embodiments octanoic acid may be preferred.

In some embodiments, the concentrated liquid composition comprises the $C_5$ to $C_{10}$ carboxylic acid, preferably octanoic acid, in an amount of about >0 wt.-% to about ≤10 wt.-%, preferably about ≥0.01 wt.-% to about ≤5 wt.-%, further preferred about ≥0.1 wt.-% to about ≤2 wt.-%, in addition preferred about ≥0.2 wt.-% to about ≤1 wt.-%, and also preferred about ≥0.3 wt.-% to about ≤0.7 wt.-%, based on the total weight of the concentrated liquid composition.

$C_5$ to $C_{10}$ Percarboxylic Acid/$C_5$ to $C_{10}$ Carboxylic Acid

According to a further embodiment the concentrated liquid composition comprises the $C_5$ to $C_{10}$ percarboxylic acid, preferably peroctanoic acid, in an amount of about ≥0.001 wt.-% to about ≤8 wt.-%, preferably about ≥0.01 wt.-% to about ≤6 wt.-%, further preferred about ≥0.1 wt.-% to about ≤1 wt.-%, also preferred about ≥0.2 wt.-% to about ≤0.5 wt.-%, based on the total weight of the concentrated liquid composition; and/or $C_5$ to $C_{10}$ carboxylic acid, preferably octanoic acid, in an amount of about >0 wt.-% to about ≤10 wt.-%, preferably about ≥0.01 wt.-% to about ≤5 wt.-%, about ≥0.2 wt.-% to about ≤1 wt.-%, in addition preferred ≥0.3 wt.-% to about ≤0.7 wt.-%, based on the total weight of the concentrated liquid composition.

Peroxide Agent

In some embodiments, the peroxide agent—also referred to as an active oxygen source herein—includes at least one peroxygen compound. Exemplary peroxygen compounds for use in the concentrated liquid composition of the present invention include hydrogen peroxide, a perborate, a percarbonate and mixtures and derivatives thereof, and preferably hydrogen peroxide. In some embodiments, the active oxygen source includes hydrogen peroxide.

The peroxide agent is different to the $C_1$ to $C_{10}$ percarboxylic acids. Preferably, the peroxide agent is not a percarboxylic acid.

In some embodiments the concentrated liquid compositions comprises about ≥5 wt.-% to about ≤30 wt.-%, preferably about ≥7 wt.-% to about ≤25 wt.-%, further preferred ≥12 wt.-% to about ≤20 wt.-%, and also preferred ≥16 wt.-% to about ≤18 wt.-% of at least one peroxide agent, preferably hydrogen peroxide.

Acidulant

In some embodiments, the concentrated liquid compositions for use with the methods of the present invention may include at least one additional acidulant. The additional acidulant can be selected from the group consisting of sulfuric acid, caprylic acid, sodium bisulfate, nitric acid, hydrochloric acid, methane sulfonic acid, ethane sulfonic acid, propane sulfonic acid, butane sulfonic acid, formic acid, acetic acid, halocarboxylic acids, picolinic acid, dipicolinic acid, and mixtures thereof, and preferably sulfuric acid.

The additional acidulant is different to the selected $C_1$ to $C_{10}$ percarboxylic acid. The additional acidulant is different to the selected $C_1$ to $C_5$ percarboxylic acid. The additional acidulant is different to the selected $C_1$ to $C_{10}$ carboxylic acid. The additional acidulant is different to the selected $C_1$ to $C_5$ carboxylic acid. In some embodiments, the acidulant is neither a carboxylic acid nor a percarboxylic acid.

In some embodiments, the amount of acidulant of the concentrated liquid composition may be ≥0 wt.-% to about ≤20 wt.-%, preferably about ≥5 wt.-% to about ≤15 wt.-%, or about ≥10 wt.-% to about ≤12 wt.-%.

Hydrotropes

In addition, various other additives or adjuvants may be present in concentrated liquid compositions of the present invention to provide additional desired properties, either of form, functional or aesthetic nature, for example:

a) Solubilizing intermediaries called hydrotropes may be present in the concentrated liquid compositions of the invention of such as an aromatic hydrocarbon sulfonate, preferably xylene sulfonate, toluene sulfonate, or cumene sulfonate; or n-octane sulfonate; or their sodium-, potassium- or ammonium salts or as salts of organic ammonium bases. Also commonly used are polyols containing only carbon, hydrogen and oxygen atoms. They preferably contain from about 2 to about 6 carbon atoms and from about 2 to about 6 hydroxy groups. Examples include 1,2-propanediol, 1,2-butanediol, hexylene glycol, glycerol, sorbitol, mannitol, and glucose.

b) Nonaqueous liquid carriers or solvents may be used for varying compositions of the present invention.

c) Viscosity modifiers may be added to the compositions of the present invention. These may include natural polysaccharides such as xanthan gum, carrageenan and the like; or cellulosic type thickeners such as carboxymethyl cellulose, and hydroxymethyl-, hydroxyethyl-, and hydroxypropyl cellulose; or, polycarboxylate thickeners such as high molecular weight polyacrylates or carboxyvinyl polymers and copolymers; or, naturally occurring and synthetic clays; and finely divided fumed or precipitated silica, to list a few. In some embodiments, the concentrated liquid compositions of use with the methods of the present invention do not include a gelling agent.

In some preferred embodiments the hydrotrope may be selected from the group comprising of a xylene sulfonate, toluene sulfonate, or cumene sulfonate, n-octane sulfonate, and/or acids thereof and also preferred cumene sulfonate.

In some embodiments, sodium-cumolsulfonate, linear alkylbenzene sulphonates (LAS) and/or xylene sulfonate, cumolsulfonate may be suitable to use as hydrotrope and having an improved solubilizing effect.

In some embodiments, the amount of hydrotrope of a concentrated liquid compositions may be $\geq 0$ wt.-% to about $\leq 20$ wt.-%, preferably about $\geq 5$ wt.-% to about $\leq 18$ wt.-%, further preferred about $\geq 8$ wt.-% to about $\leq 15$ wt.-%, and in addition preferred about $\geq 10$ wt.-% to about $\leq 12$ wt.-%.

Builders

In some embodiments, the concentrated liquid compositions for use with the methods of the present invention may include a builder or builders. The builder is different to the carbonic acids and peroxycarbonic acids and different to the acidulants. Further, the builder is different to the chelants.

Builders include sequestering agents (sequestrants), detergent builders, and the like. The builder often stabilizes the composition or solution. In some embodiments, builders suitable for use with the methods of the present invention preferably do not complex with the activator complex. That is, the builder or builders for use with the present invention are selected such that they preferentially complex with the mineral soil broken up after the oxygen gas has been generated in situ on and in the soil, rather than with the activator complex.

Builders and builder salts may be inorganic or organic. Examples of builders suitable for use with the methods of the present invention include, but are not limited to, aminocarboxylates and their derivatives, pyrophosphates, polyphosphates, ethylenediamene and ethylenetriamene derivatives, hydroxyacids, and mono-, di-, and tri-carboxylates and their corresponding acids. Other builders include aluminosilicates, nitroloacetates and their derivatives, and mixtures thereof. Still other builders include aminocarboxylates, including salts of hydroxyethylene-diaminetetraacetic acid (HEDTA), and diethylenetriaminepentaacetic acid.

In some embodiments, a biodegradable aminocarboxylate or derivative thereof is present as a builder in the methods of the present invention. Exemplary biodegradable aminocarboxylates include, but are not limited to: Dissolvine GL-38® and Dissolvine GL-74 ® both available from Akzo; Trilon M® available from BASF; Baypure CX100® available from Bayer; Versene EDG® available from Dow; HIDS® available from Nippon Shakubai; Octaquest E30® and Octaquest A65® both available from Finetex/Innospec Octel.

In some embodiments, an organic builder agent may be used. Organic builder agents include both polymeric and small molecule builder agents. Organic small molecule builder agents are typically organocarboxylate compounds. Polymeric builder agents commonly include polyanionic compositions such as polyacrylic acid compounds. Small molecule organic chelating agents include N-hydroxyethylenediaminetriacetic acid (HEDTA), ethylenediaminetetraacetic acid (EDTA), nitrilotriaacetic acid (NTA), diethylenetriaminepentaacetic acid (DTPA), ethylenediaminetetraproprionic acid triethylenetetraaminehexaacetic acid (TTHA), and the respective alkali metal, ammonium and substituted ammonium salts thereof.

Other suitable builder includes water soluble polycarboxylate polymers. Such homopolymeric and copolymeric builder agents include polymeric compositions with pendant (—$CO_2H$) carboxylic acid groups and include polyacrylic acid, polymethacrylic acid, polymaleic acid, acrylic acid-methacrylic acid copolymers, acrylic-maleic copolymers, hydrolyzed polyacrylamide, hydrolyzed methacrylamide, hydrolyzed acrylamide-methacrylamide copolymers, hydrolyzed polyacrylonitrile, hydrolyzed polymethacrylonitrile, hydrolyzed acrylonitrile methacrylonitrile copolymers, or mixtures thereof. Water soluble salts or partial salts of these polymers or copolymers such as their respective alkali metal (for example, sodium or potassium) or ammonium salts may also be used. The weight average molecular weight of the polymers is from about 4000 to about 12,000. Preferred polymers include polyacrylic acid, the partial sodium salts of polyacrylic acid or sodium polyacrylate having an average molecular weight within the range of 4000 to 8000.

Preferred builders for use with the methods of the present invention are water soluble. Water soluble inorganic alkaline builder salts which may be used alone or in admixture with other builders include, but are not limited to, alkali metal or ammonia or substituted ammonium salts of carbonates, silicates and borates. Water soluble organic alkaline builders which are useful in the present invention include alkanolamines and cyclic amines.

Particularly preferred builders include polyacrylic acid (PAA) and its salts, ethylenediaminetetraacetic acid (EDTA) and sodium gluconate.

In some embodiments, the builder may be a polyacrylic acid, ethylenedinitrilotetra-acetic acid, gluconic acid and/or salts thereof.

In some embodiments, the amount of builder present in the concentrated compositions for use with the methods of the present invention is about $\geq 0$ wt.-% to about $\leq 10$ wt.-%, preferably about 0.001 wt % to about 5 wt %.

Chelants

In some embodiments, the concentrated liquid compositions for use with the methods of the present invention may include at least one chelant.

In peroxide formulations, some metal ions, especially heavy metals, have the tendency to enhance reaction of the peroxide agent causing peroxide decomposition. The addition of chelants that traps heavy metal ions can increase stability of the peroxide agents. In case components are used having a high purity grade, the addition of a chelant is not necessary.

Exemplary commercially available chelating agents for use with the methods of the present invention include, but are not limited to: sodium tripolyphosphate available from Innophos; Trilon A® available from BASF; Versene 100®, Low NTA Versene®, Versene Powder®, and Versenol 120® all available from Dow; Dissolvine D-40 available from BASF; and sodium citrate.

In some embodiments, dipicolinic acid and/or phosphonic acid and corresponding salts thereof are suitable for use as chelating agents with the methods of the invention.

Phosphonates are suitable for use as chelating agents with the methods of the invention and can be selected from the group comprising 2-aminoethylphosphonic acid (AEPn); dimethyl methylphosphonate (DMMP); 1-hydroxy ethylidene-1,1-diphosphonic acid (HEDP); amino tris(methylene phosphonic acid) (ATMP); ethylenediamine tetra(methylene phosphonic acid) (EDTMP); tetramethylenediamine tetra (methylene phosphonic acid) TDTMP); hexamethylenediamine tetra(methylene phosphonic acid) (HDTMP); diethylenetriamine penta(methylene phosphonic acid) (DTPMP); phosphonobutane-tricarboxylic acid (PBTC); N-(phosphonomethyl)iminodiacetic acid (PMIDA); 2-carboxyethyl phosphonic acid (CEPA); 2-hydroxyphosphonocarboxylic acid (HPAA); amino-tris-(methylene-phosphonic acid) (AMP); and/or salts thereof.

Aminophosphonates are also suitable for use as chelating agents with the methods of the invention and include ethylenediaminetetramethylene phosphonates, nitrilotrismethylene phosphonates, and diethylenetriamine-(pentamethylene phosphonate) for example. These aminophosphonates commonly contain alkyl or alkenyl groups with less than 8 carbon atoms.

In some embodiments, the amount of chelant is about ≥0 wt.-% to about ≤10 wt.-%, preferably about ≥0.1 wt.-% to about ≤5 wt.-%, further preferred ≥0.3 wt.-% to about ≤2.5 wt.-%, and also preferred ≥0.5 wt.-% to about ≤1 wt.-%, of a chelant, preferably dipicolinic acid and/or a phosphonic acid and also preferred a 1-hydroxyethane-(1,1-diphosphonic acid) (HEDP).

Surfactants

In some embodiments, the concentrated liquid composition as well as the use composition may contain an additional surfactant.

In some also preferred embodiments, the concentrated liquid composition as well as the use composition according to the invention contain no additional surfactant.

Additional Components

Exemplary additional components that may be provided within the compositions used in the methods of the present invention may include at least one chelant, builder, water conditioning agents, non-aqueous components, adjuvants, carriers, processing aids, enzymes, penetrants, antimicrobial agents, buffers, and pH adjusting agents. However, the concentrated liquid composition as well as the use composition according to the invention can be free of additional builders, water conditioning agents, non-aqueous components, adjuvants, carriers, processing aids, enzymes, penetrants, antimicrobial agents, buffers, and pH adjusting agents.

In some embodiments, the concentrated liquid composition as well as the use composition according to the invention can contain phosphonate or is free of phosphonate.

In some embodiments, the concentrated liquid composition as well as the use composition according to the invention can contain a chelant, such as phosphonate and a builder.

In some embodiments, the concentrated liquid composition as well as the use composition according to the invention can contain a chelant, such as phosphonate and is free of a builder.

In some embodiments, the concentrated liquid composition as well as the use composition according to the invention is free of phosphonate and a builder.

In some embodiments, the concentrated liquid composition as well as the use composition according to the invention can contain a chelant such as phosphonate and optional a builder, wherein the builder is selected from the group comprising polyacrylic acid (PAA) and its salts, ethylenediaminetetraacetic acid (EDTA) and sodium.

In some embodiments, the concentrated liquid composition as well as the use composition according to the invention can contain a chelant, for example a phosphonate, wherein the phosphonate is preferably 1-hydroxyethylidene-1,1-diphosphonic Acid (HEDP).

Penetrants

In some embodiments, a penetrant may be used with the methods of the present invention. The penetrant may be combined with an alkaline source in the cleaning composition, or, the penetrant may be used without an alkaline source. In some embodiments, the penetrant is water miscible.

Examples of suitable penetrants include, but are not limited to, alcohols, short chain ethoxylated alcohols and phenol (having 1-6 ethoxylate groups). Organic solvents are also suitable penetrants. Examples of suitable organic solvents, for use as a penetrant, include esters, ethers, ketones, amines, and nitrated and chlorinated hydrocarbons.

Ethoxylated alcohols are also suitable for use with the methods of the present invention. Examples of ethoxylated alcohols include, but are not limited to, alky, aryl, and alkylaryl alkloxylates. These alkloxylates may be further modified by capping with chlorine-, bromine-, benzyl-, methyl-, ethyl-, propyl-, butyl- and alkyl-groups. Ethoxylated alcohols may be present in the cleaning composition from about 0.1 wt % to about 20 wt %.

Fatty acids are also suitable for use as penetrants in the methods of the present invention. Some non-limiting examples of fatty acids are $C_6$ to $C_{12}$ straight or branched fatty acids. In some embodiments, fatty acids used in the methods of the present invention are liquid at room temperature.

In some embodiments, a penetrant for use in the methods of the present invention includes water soluble glycol ethers. Examples of glycol ethers include dipropylene glycol methyl ether (available under the trade designation DOWANOL DPM from Dow Chemical Co.), diethylene glycol methyl ether (available under the trade designation DOWANOL DM from Dow Chemical Co.), propylene glycol methyl ether (available under the trade designation DOWANOL PM from Dow Chemical Co.), and ethylene glycol monobutyl ether (available under the trade designation DOWANOL EB from Dow Chemical Co.).

Storage Stable, Concentrated Liquid Composition

The composition of the invention can be provided in the form of a concentrated liquid composition.

In some embodiments the concentrated liquid compositions may be obtained by mixing:
- about ≥0.01 wt.-% to about ≤25 wt.-%, preferably about ≥0.05 wt.-% to about ≤15 wt.-%, further preferred about ≥0.1 wt.-% to about ≤10 wt.-%, in addition preferred about ≥0.2 wt.-% to about ≤1 wt.-%, and also preferred about ≥0.3 wt.-% to about ≤0.5 wt.-%, of at least one C6 to C22 sulfocarboxylic acid, preferably sulphonated oleic acid;
- about ≥10 wt.-% to about ≤50 wt.-%, preferably about ≥15 wt.-% to about ≤40 wt.-%, further preferred ≥18 wt.-% to about ≤30 wt.-%, and also preferred ≥20 wt.-% to about ≤27 wt.-%, of a C1 to C4 carboxylic acid, preferably acetic acid;
- about >0 wt.-% to about ≤10 wt.-%, preferably about ≥0.01 wt.-% to about ≤5 wt.-%, further preferred about ≥0.1 wt.-% to about ≤2 wt.-%, and also preferred about ≥0.2 wt.-% to about ≤1 wt.-%, and also preferred ≥0.3 wt.-% to about ≤0.7 wt.-%, of at least one $C_5$ to $C_{10}$ carboxylic acid, preferably octanoic acid;
- about ≥5 wt.-% to about ≤30 wt.-%, preferably about ≥7 wt.-% to about ≤25 wt.-%, further preferred ≥12 wt.-% to about ≤20 wt.-%, and also preferred ≥16 wt.-% to about ≤18 wt.-% of at least one peroxide agent, preferably hydrogen peroxide;
- about ≥0 wt.-% to about ≤20 wt.-%, preferably about ≥5 wt.-% to about ≤15 wt.-%, and also preferred about ≥10 wt.-% to about ≤12 wt.-%, of at least one acidulant, preferably sulfuric acid;
- about ≥0 wt.-% to about ≤20 wt.-%, preferably about ≥5 wt.-% to about ≤18 wt.-%, and further preferred about ≥8 wt.-% to about ≤15 wt.-%, and in addition preferred about ≥10 wt.-% to about ≤12 wt.-%, of a hydrotrope, preferably selected from the group comprising of a xylene sulfonate, toluene sulfonate, or cumene sulfonate, n-octane sulfonate, and/or acids thereof and also preferred cumene sulfonate;
- about ≥0 wt.-% to about ≤10 wt.-%, preferably about ≥0.1 wt.-% to about ≤5 wt.-%, further preferred ≥0.3 wt.-% to about ≤2.5 wt.-%, and also preferred ≥0.5 wt.-% to about ≤1 wt.-%, of a chelant, preferably dipicolinic acid and/or a phosphonic acid and also preferred a 1-hydroxyethane-(1,1-diphosphonic acid) (HEDP); and
- a solvent, preferably water, wherein the components are selected such that the total weight amount of all components of the concentrated liquid composition is 100 wt.-%.

In some embodiments the concentrated liquid compositions comprises:
- about ≥0.001 wt.-% to about ≤2 wt.-%, preferably about ≥0.01 wt.-% to about ≤1.5 wt.-%, further preferred ≥0.03 wt.-% to about ≤1 wt.-%, and also preferred ≥0.05 wt.-% to about ≤0.1 wt.-%, of at least one C6 to C22 sulfoperoxycarboxylic acid, preferably sulphonated peroxyoleic acid;
- about ≥0.01 wt.-% to about ≤25 wt.-%, preferably about ≥0.05 wt.-% to about ≤15 wt.-%, further preferred about ≥0.1 wt.-% to about ≤10 wt.-%, additionally preferred ≥0.2 wt.-% to about ≤1 wt.-%, and also preferred about ≥0.3 wt.-% to about ≤0.5 wt.-%, of at least one C6 to C22 sulfocarboxylic acid, preferably sulphonated oleic acid;
- about ≥2.5 wt.-% to about ≤16.5 wt.-%, preferably about ≥5 wt.-% to about ≤16 wt.-%, further preferred about ≥6 wt.-% to about ≤15 wt.-%, and also preferred ≥7 wt.-% to about ≤13.5 wt.-%, of a $C_1$ to $C_4$ percarboxylic acid, preferably peracetic acid;
- about ≥10 wt.-% to about ≤50 wt.-%, preferably about ≥15 wt.-% to about ≤40 wt.-%, further preferred ≥18 wt.-% to about ≤30 wt.-%, and also preferred ≥20 wt.-% to about ≤27 wt.-%, of a C1 to C4 carboxylic acid, preferably acetic acid;
- about ≥0 wt.-% to about ≤8 wt.-%, preferably about ≥0.001 wt.-% to about ≤6 wt.-%, further preferred about ≥0.01 wt.-% to about ≤2 wt.-%, in addition preferred ≥0.1 wt.-% to about ≤1 wt.-%, and also preferred ≥0.2 wt.-% to about ≤0.5 wt.-%, of at least one C5 to C10 percarboxylic acid, preferably peroxyoctanoic acid;
- about >0 wt.-% to about ≤10 wt.-%, preferably about ≥0.01 wt.-% to about ≤5 wt.-%, further preferred ≥0.1 wt.-% to about ≤2 wt.-%, in addition preferred ≥0.2 wt.-% to about ≤1 wt.-%, and also preferred ≥0.3 wt.-% to about ≤0.7 wt.-%, of a $C_5$ to $C_{10}$ carboxylic acid, preferably octanoic acid;
- about ≥5 wt.-% to about ≤30 wt.-%, preferably about ≥7 wt.-% to about ≤25 wt.-%, further preferred ≥12 wt.-% to about ≤20 wt.-%, and also preferred ≥16 wt.-% to about ≤18 wt.-% of at least one peroxide agent, preferably hydrogen peroxide;
- about ≥0 wt.-% to about ≤20 wt.-%, preferably about ≥5 wt.-% to about ≤18 wt.-%, or about ≥8 wt.-% to about ≤15 wt.-%, and in addition preferred about ≥10 wt.-% to about ≤12 wt.-%, of a hydrotrope, preferably selected from the group comprising of a xylene sulfonate, toluene sulfonate, or cumene sulfonate, n-octane sulfonate, and/or acids thereof and also preferred cumene sulfonate;
- about ≥0 wt.-% to about ≤10 wt.-%, preferably about ≥0.1 wt.-% to about ≤5 wt.-%, further preferred ≥0.3 wt.-% to about ≤2.5 wt.-%, and also preferred ≥0.5 wt.-% to about ≤1 wt.-%, of a chelant, preferably dipicolinic acid and/or a phosphonic acid and also preferred a 1-hydroxyethane-(1,1-diphosphonic acid) (HEDP);
- about ≥0 wt.-% to about ≤20 wt.-%, preferably about ≥5 wt.-% to about ≤15 wt.-%, and also preferred about ≥10 wt.-% to about ≤12 wt.-%, of at least one acidulant, preferably sulfuric acid; and
- a solvent, preferably water, wherein the components are selected such that the total weight amount of all components of the concentrated liquid composition is 100 wt.-%.

In some embodiments, the concentrated composition comprises an additional acidulant.

In some other embodiments, the concentrated composition is free of an additional acidulant.

In some embodiments, the concentrated composition comprises an additional surfactant.

In some other embodiments, the concentrated composition is free of an additional surfactant.

In some embodiments, the concentrated composition comprises an additional surfactant and an additional acidulant.

In some other embodiments, the concentrated composition is free of an additional surfactant and an additional acidulant.

In some embodiments, the concentrated composition comprises an additional surfactant, an additional acidulant and an additional builder.

In some other embodiments, the concentrated composition is free of an additional surfactant, an additional acidulant and an additional builder.

Use Compositions

The concentrated liquid composition can be further diluted in order to obtain a use composition that can be directly used in a clean in place (CIP), clean out of place (CIP) process and/or in particular in the field of cold-aseptic filling (CAF).

According to some preferred embodiment the use composition can be used in the field of cold aseptic filling (CAF), for example in the beverage and dairy industry.

According to some embodiments the use composition can be used for cleaning and/or disinfecting of tanks, lines, pumps and other process equipment used for processing typically liquid product streams of beverages, such as fruit juices, tea beverages, sports drinks, vegetable juices, milk-based mixed drinks, UHT milk, near-water drinks and flavored waters. It can be used for both still and carbonated beverages.

In some embodiments the use composition may be obtained by diluting a concentrated liquid composition of the invention with a solvent, preferably water, in a ratio of concentrated composition to solvent, for example water, of about 1:5000 to 1:10, preferably of about 1:1000 to 1:50, in particular of about 1:500 to 1:100, and also preferred of about 1:100 to 1:250.

In some embodiments, the use composition comprises a mixture of:
a) a C6 to C22 sulfoperoxycarboxylic acid,
b) a $C_1$ to $C_4$ percarboxylic acid,
c) a $C_5$ to $C_{10}$ percarboxylic acid,
d) a peroxide agent,
e) optional a hydrotrope,
f) optional a chelant, preferably dipicolinic acid and/or a phosphonic acid;
g) a liquid; wherein the use composition comprises free C6 to C22 sulfocarboxylic acid, free $C_1$ to $C_4$ carboxylic acid and free $C_5$ to $C_{10}$ carboxylic acid, wherein the weight ratio of C6 to C22 sulfocarboxylic acid to C6 to C22 sulfoperoxycarboxylic acid is about 0.1:1 to about 25:1.

In some embodiments of the use composition the content of the $C_1$ to $C_4$ percarboxylic acid is ≥0.0125 wt.-% to ≤1.6 wt.-% and the content of the $C_5$ to $C_{10}$ percarboxylic acid is >0.000005 wt.-% to ≤0.8 wt.-%, based on the total weight of the use composition.

In some embodiments the use compositions may be obtained by mixing a) the concentrated liquid compositions with b) a solvent of:
a) concentrated liquid compositions comprising:
about ≥0.01 wt.-% to about ≤25 wt.-%, preferably about ≥0.05 wt.-% to about ≤15 wt.-%, further preferred about ≥0.1 wt.-% to about ≤10 wt.-%, additionally preferred about ≥0.2 wt.-% to about ≤1 wt.-%, and also preferred about ≥0.3 wt.-% to about ≤0.5 wt.-%, of at least one C6 to C22 sulfocarboxylic acid, preferably sulphonated oleic acid;
about ≥10 wt.-% to about ≤50 wt.-%, preferably about ≥15 wt.-% to about ≤40 wt.-%, further preferred ≥18 wt.-% to about ≤30 wt.-%, and also preferred ≥20 wt.-% to about ≤27 wt.-%, of a C1 to C4 carboxylic acid, preferably acetic acid;
about >0 wt.-% to about ≤10 wt.-%, preferably about ≥0.01 wt.-% to about ≤5 wt.-%, further preferred about ≥0.1 wt.-% to about ≤2 wt.-%, and also preferred about ≥0.5 wt.-% to about ≤2 wt.-%, additionally preferred about ≥0.2 wt.-% to about ≤1 wt.-%, and also preferred ≥0.3 wt.-% to about ≤0.7 wt.-%, of at least one $C_5$ to $C_{10}$ carboxylic acid, preferably octanoic acid;
about ≥5 wt.-% to about ≤30 wt.-%, preferably about ≥7 wt.-% to about ≤25 wt.-%, further preferred ≥12 wt.-% to about ≤20 wt.-%, and also preferred ≥16 wt.-% to about ≤18 wt.-% of at least one peroxide agent, preferably hydrogen peroxide;
about ≥0 wt.-% to about ≤20 wt.-%, preferably about ≥5 wt.-% to about ≤18 wt.-%, or about ≥8 wt.-% to about ≤15 wt.-%, and in addition preferred about ≥10 wt.-% to about ≤12 wt.-%, of a hydrotrope, preferably selected from the group comprising of a xylene sulfonate, toluene sulfonate, cumene sulfonate, n-octane sulfonate, and/or acids thereof and also preferred cumene sulfonate;
about ≥0 wt.-% to about ≤10 wt.-%, preferably about ≥0.1 wt.-% to about ≤5 wt.-%, further preferred ≥0.3 wt.-% to about ≤2.5 wt.-%, and also preferred ≥0.5 wt.-% to about ≤1 wt.-%, of a chelant, preferably dipicolinic acid and/or a phosphonic acid and also preferred a 1-hydroxyethane-(1,1-diphosphonic acid) (HEDP);
about ≥0 wt.-% to about ≤20 wt.-%, preferably about ≥5 wt.-% to about ≤15 wt.-%, and also preferred about ≥10 wt.-% to about ≤12 wt.-%, of at least one acidulant, preferably sulfuric acid; and
a solvent, preferably water, wherein the components are selected such that the total weight amount of all components of the concentrated liquid composition is 100 wt.-%; with
b) a solvent, for example water, wherein
the ratio of a) concentrated liquid composition to b) solvent is of about 1:5000 to 1:10, preferably of about 1:1000 to 1:50, in particular of about 1:500 to 1:100, and also preferred of about 1:100 to 1:250.

In some embodiments a use compositions comprises:
about ≥0.000005 wt.-% to about ≤0.2 wt.-%, preferably about ≥0.00005 wt.-% to about ≤0.15 wt.-%, further preferred about ≥0.00015 wt.-% to about ≤0.1 wt.-%, and also preferred about ≥0.00025 wt.-% to about ≤0.01 wt.-%, of at least one C6 to C22 sulfoperoxycarboxylic acid, preferably sulphonated peroxyoleic acid;
about ≥0.00005 wt.-% to about ≤2.5 wt.-%, preferably about ≥0.00025 wt.-% to about ≤1.5 wt.-%, further preferred about ≥0.0005 wt.-% to about ≤1 wt.-%, and also preferred about ≥0.001 wt.-% to about ≤0.1 wt.-%, and also preferred about ≥0.0015 wt.-% to about ≤0.05 wt.-%, of at least one C6 to C22 sulfocarboxylic acid, preferably sulphonated oleic acid;
about ≥0.0125 wt.-% to about ≤1.65 wt.-%, preferably about ≥0.025 wt.-% to about ≤1.5 wt.-%, further preferred about ≥0.03 wt.-% to about ≤1.0 wt.-%, and also preferred ≥0.035 wt.-% to about ≤0.8 wt.-%, of a $C_1$ to $C_4$ percarboxylic acid, preferably peracetic acid;
about ≥0.05 wt.-% to about ≤5 wt.-%, preferably about ≥0.075 wt.-% to about ≤4 wt.-%, further preferred about ≥0.09 wt.-% to about ≤3 wt.-%, and also preferred about ≥0.1 wt.-% to about ≤2.5 wt.-%, of a $C_1$ to $C_4$ carboxylic acid, preferably acetic acid;
about >0 wt.-% to about ≤0.8 wt.-%, preferably about ≥0.000005 wt.-% to about ≤0.6 wt.-%, further preferred about ≥0.00005 wt.-% to about ≤0.2 wt.-%, in addition preferred ≥0.0005 wt.-% to about ≤0.1 wt.-%, and also preferred ≥0.001 wt.-% to about ≤0.04 wt.-%, of at least one $C_5$ to $C_{10}$ percarboxylic acid, preferably peroxyoctanoic acid;
about >0 wt.-% to about ≤1 wt.-%, preferably about ≥0.00005 wt.-% to about ≤0.5 wt.-%, further preferred about ≥0.0005 wt.-% to about ≤0.2 wt.-%, and also preferred ≥0.001 wt.-% to about ≤0.1 wt.-%, and also preferred ≥0.0015 wt.-% to about ≤0.07 wt.-%, of at least one $C_5$ to $C_{10}$ carboxylic acid, preferably octanoic acid;

about ≥0.025 wt.-% to about ≤3 wt.-%, preferably about ≥0.06 wt.-% to about ≤2.5 wt.-%, further preferred about ≥0.075 wt.-% to about ≤2 wt.-%, and also preferred about ≥0.08 wt.-% to about ≤1.8 wt.-%, of at least one peroxide agent, preferably hydrogen peroxide;

about ≥0 wt.-% to about ≤2 wt.-%, preferably about ≥0.025 wt.-% to about ≤1.8 wt.-%, further preferred about ≥0.04 wt.-% to about ≤1.5 wt.-%, and also preferred about ≥0.05 wt.-% to about ≤1.2 wt.-%, of a hydrotrope, preferably selected from the group comprising of a xylene sulfonate, toluene sulfonate, or cumene sulfonate, n-octane sulfonate, and/or acids thereof and also preferred cumene sulfonate;

about ≥0 wt.-% to about ≤1 wt.-%, preferably about ≥0.0005 wt.-% to about ≤0.5 wt.-%, further preferred ≥0.0015 wt.-% to about ≤0.25 wt.-%, and also preferred ≥0.0025 wt.-% to about ≤0.1 wt.-%, of a chelant, preferably dipicolinic acid and/or a phosphonic acid and also preferred a 1-hydroxyethane-(1,1-diphosphonic acid) (HEDP);

about ≥0 wt.-% to about ≤2 wt.-%, preferably about ≥0.025 wt.-% to about ≤1.5 wt.-%, and also preferred about ≥0.05 wt.-% to about ≤1.2 wt.-%, of at least one acidulant, preferably sulfuric acid a liquid, preferably water; wherein the components are selected such that the total weight amount of all components of the concentrated liquid composition is 100 wt.-%.

In some embodiments, the use composition comprises an additional acidulant. In some other embodiments, the use composition is free of an additional acidulant.

In some embodiments, the use composition comprises an additional surfactant. In some other embodiments, the use composition is free of an additional surfactant.

In some embodiments, the use composition comprises an additional surfactant and an additional acidulant. In some other embodiments, the use composition is free of an additional surfactant and an additional acidulant.

In some embodiments, the use composition comprises an additional surfactant, an additional acidulant and an additional builder. In some other embodiments, the use composition is free of an additional surfactant, an additional acidulant and an additional builder.

Methods of Cleaning

In some embodiments, the present invention provides methods for disinfection of a surface, preferably hard surfaces.

In some embodiments, the methods for disinfection of a surface include disinfection processes in the field of cold aseptic filling (CAF), clean out of place (COP) or clean in place (CIP).

In some other embodiments, the present invention provides methods for removing soil from a surface.

In some embodiments, the methods for removing soil from a surface include cleaning processes in the field of cold aseptic filling (CAF), clean out of place (COP) or clean in place (CIP).

In some embodiments, the present invention provides methods for removing soil from a surface and disinfection.

In some further embodiments, the methods for removing soil and disinfection from a surface include using composition of the invention in the process of cold aseptic filling (CAF), in a clean out of place (COP) or clean in place (CIP).

The methods include applying to the surface a composition of the invention, preferably in form of use solution. A use solution means a composition that can be applied on the surfaces to be cleaned and/or disinfected without further dilution thereof.

However, in some embodiments a concentrated liquid composition is used that can be further diluted, for example at the place that has to be cleaned, bleached and/or disinfected.

According to one aspect the composition of the invention, preferably the use composition, can be used for cleaning and/or disinfecting of surfaces, preferably in the food and beverage industry, also preferred for cleaning and/or disinfecting in the field of cold aseptic filling.

Exemplary industries in which the methods and compositions of the present invention may be used include, but are not limited to: the food and beverage industry, e.g., the milk, dairy, cheese, sugar, and brewery industries; oil processing industry; industrial agriculture and ethanol processing; and the pharmaceutical manufacturing industry.

According to a further aspect the composition, preferably the use composition, can be used for reduction of bacterial and/or bacterial spores, preferably with a log reduction of about ≥3 log. The bacterial and/or bacterial spores can be selected for example from the group comprising *Bacillus athrophaeus, Bacillus cereus, Bacillus subtilis, Chaetomium globosum* and/or *Paenibacillus chibensis*.

Surfaces

In some embodiments, the methods and compositions of the present invention, for example the use composition, are applied to surfaces for disinfection and/or cleaning, such as hard and/or soft surfaces, for example of upper outer and/or inner outer surfaces of materials such as ceramic, metal, plastic and/or glass, surfaces that came into contact with beverages and/or food, beverages such alcoholic or non-alcoholic beverages such as beer or milk, food such as meat, vegetables and/or grain-products.

Other surfaces that can be disinfected and/or cleaned are instruments and apparatus, for example used in sanitary or medical services, evaporators, heat exchangers, including tube-in-tube exchangers, direct steam injection, and plate-in-frame exchangers, heating coils including steam, flame or heat transfer fluid heated re-crystallizers, pan crystallizers, spray dryers, drum dryers, bottles and tanks.

Additional surfaces capable of being disinfected and/or cleaned using the methods and compositions of the present invention include, but are not limited to membranes, medical devices, laundry and/or textiles, and hard surfaces, e.g., walls, floors, dishes, flatware, pots and pans, heat exchange coils, ovens, fryers, smoke houses, sewer drain lines, and vehicles. In some embodiments, the surfaces may be cleaned using a clean in place method. The methods of the present invention may also be used to remove dust from air handling equipment, for example, from air conditioners and refrigeration heat exchangers. In other embodiments, the methods of the present invention may be used for drain line microbial control, e.g., to reduce or remove biofilm formation.

Temperature

The methods and compositions of the present invention for cleaning, and/or disinfecting from surfaces can be used at reduced temperatures, e.g., from about ≥0° C. to about ≤80° C., preferably at about ≥40° C. to about ≤60° C. The composition of the invention has an increased cleaning, and in particular disinfecting activity compared to conventional compositions, e.g. used in the field of cold aseptic filling (CAF).

The ability to use the composition according to the invention at reduced temperatures, preferably at about ≤60° C. results in energy and cost savings compared to traditional cleaning techniques that require increased temperatures.

It has also been found that the composition of the present invention provide for cleaning and/or disinfecting need reduced amounts of chemistry, compared to conventional cleaning compositions. In some embodiments, the methods of the present invention use about 20% to about 70% less active components, than standard peracid compositions used in conventional cleaning methods. Thus, the methods of the present invention may effectively remove soil, bleach and/or disinfect surfaces at reduced temperatures, and using a low concentration of chemicals, providing both an energy savings and a reduction in the amount of chemistry consumed per cleaning.

Time

In some embodiments of the invention, the concentrated liquid compositions for use with the methods of the present invention are applied as concentrated composition or in the form of a use composition, i.e. the concentrated composition is diluted further to a use composition that can be direct applied without further treatment to the surface to be cleaned.

peracetic, peroctanoic acid and C6 to C22 sulfoperoxycarboxylic acids compared to the same composition C, D, E and F of table 1 comprising peracetic acid and/or peroctanoic acid.

Rinsing

It has been surprisingly found that the number of rinsing steps to achieve the surface tension of water is remarkable low for a use composition of the present invention composition A and B of table 1 comprising peracetic, peroctanoic acid and C6 to C22 sulfoperoxycarboxylic acids compared to the same composition C, D, E and F of table 1 comprising peracetic acid and/or peroctanoic acid.

Wetting and Rinsing Test

The compositions of A to F were prepared 24 hours before the test and tempered up to 40° C. After 24 hours at 40° C., 1 l of the composition is filed into 1 l PET-Bottle and discharged after 30 seconds. The bottle is completely filled with distilled water and discharged to its half. A sample of 100 ml was taken to measure the surface tension. The test is completed when camphor crystal move on the distilled water in the bottle or the surface tension becomes about 78 mN/m, that is an indication of "surfactant free". The numbers of rinsing steps needed to obtain "surfactant-free" was measured and given in table 1.

TABLE 1

| Components wt.-% | A | B | C | D | E | F |
|---|---|---|---|---|---|---|
| sulfonated oleic acid | 0.2 | 0.2 | — | — | — | — |
| acetic acid | 20 | 19 | 20 | 19 | — | 20 |
| peracetic acid | 7 | 8 | 7 | 8 | — | 7 |
| octanoic acid | 0.3 | 0.7 | 0.3 | 0.7 | 0.3 | — |
| peroxyoctanoic acid | 0.2 | 0.4 | 0.2 | 0.4 | 0.2 | — |
| $H_2O_2$ | 16 | 16 | 16 | 16 | 16 | 16 |
| double distilled water | add. 100 wt.-% | add. 100 wt.-% | add. 100 wt.-% | add. 100 wt.-% | add. 100 wt.-% | add. 100 wt.-% |
| surface tension [mN/m] | 78 | 75 | <70 | <70 | <70 | <70 |
| Rinsing steps | 2 | 2 | 3 | 3 | 3 | 3 |

In some embodiments, the composition, preferably the diluted composition, in particular for CAF applications, is applied to the surface to be treated for about 1 minutes to about 60 minutes, preferably about 3 minutes to about 30 minutes, further preferred about 5 minutes to about 10 minutes.

In other embodiments, the composition, preferably the diluted use composition, in particular for CAF applications, is applied to the surface for about 10 minutes to about 30 minutes. It is to be understood that all values and ranges between these values and ranges are encompassed by the methods of the present invention.

Surface Tension

It has been surprisingly found that the surface tension is remarkable low for a use composition of the present invention, e.g., composition A and B of table 1, comprising The surface tension [mN/m] of the components A and B are lower than of C, D, E and F.

It can be taken from table 1 that the number of rinsing steps with respect to components A and B necessary to reach a surface tension of about 78 mN/m (=$H_2O$) are less than compared to the compositions C, D, E and F.

Examples

The present invention is more particularly described in the following examples that are intended as illustrations only. Unless otherwise noted, all parts, percentages, and ratios reported in the following examples are on a weight basis, and all reagents used in the examples were obtained, or are available, from the chemical suppliers described below, or may be synthesized by conventional techniques.

TABLE 2

Concentrated Composition obtained by mixing the components

| Components | E1 wt.-% | E2 wt.-% | E3 wt.-% | E4 wt.-% | E5 wt.-% | E6 wt.-% |
|---|---|---|---|---|---|---|
| $H_2O$ | add. 100 wt.-% | add. 100 wt.-% | add. 100 wt.-% | add. 100 wt.-% | add. 100 wt.-% | add. 100 wt.-% |
| Acetic Acid 80% | 27.0 | 27.0 | 27.0 | 27.0 | 27.0 | 27.0 |

TABLE 2-continued

| Concentrated Composition obtained by mixing the components | | | | | | |
|---|---|---|---|---|---|---|
| Components | E1 wt.-% | E2 wt.-% | E3 wt.-% | E4 wt.-% | E5 wt.-% | E6 wt.-% |
| Octanoic Acid | 0.5 | 1.0 | 2.0 | 0.5 | 1.0 | 2.0 |
| $H_2O_2$ 50% | 40.0 | 40.0 | 40.0 | 40.0 | 40.0 | 40.0 |
| HEDP[*1] | 1.0 | 1.0 | 1.0 | — | — | — |
| Sulfocarboxylic acid[*2] | 4.0 | 4.0 | 4.0 | 4.0 | 4.0 | 4.0 |
| Cumolsulfat | 10 | 10 | 10 | 10 | 10 | 10 |
| Total | 100 wt.-% | 100 wt.-% | 100 wt.-% | 100 wt.-% | 100 wt.-% | 100 wt.-% |

[*1] = 1-Hydroxyethane-(1,1-diphosphonic acid)
[*2] = sulphonated oleic acid, preferably Lankropol OPA available from AkzoNobel Table 1: examples E1 to E6 of the invention that shows no phase separation at about 40° C. at a storage period of at least 7 days obtained by mixing the components mentioned in table 2.

TABLE 3

| Concentrated Composition obtained by mixing the components | | | | | | |
|---|---|---|---|---|---|---|
| Components | V1 wt.-% | V2 wt.-% | V3 wt.-% | V4 wt.-% | V5 wt.-% | V6 wt.-% |
| $H_2O$ | add. 100 wt.-% | add. 100 wt.-% | add. 100 wt.-% | add. 100 wt.-% | add. 100 wt.-% | add. 100 wt.-% |
| Acetic Acid 80% | 27.0 | 30.0 | 33.0 | 40.0 | 35.0 | 30.0 |
| Octanoic Acid | — | — | — | — | — | — |
| $H_2O_2$ 50% | 40 | 40 | 40 | 40.0 | 40.0 | 40.0 |
| HEDP[*1] | 1 | 1 | 1 | 1 | 1 | 1 |
| Sulfocarboxylic acid[*2] | 4.0 | 4.0 | 4.0 | 4.0 | 4.0 | 4.0 |
| Cumolsulfat | 10 | 10 | 10 | 10.0 | 10.0 | 10.0 |
| Total | 100 wt.-% | 100 wt.-% | 100 wt.-% | 100 wt.-% | 100 wt.-% | 100 wt.-% |

[*1] = 1-hydroxyethane-(1,1-diphosphonic acid)
[*2] = sulphonated oleic acid, preferably Lankropol OPA available from AkzoNobel Table 3 shows comparison examples V1 to V6 obtained by mixing the components mentioned in table 2 that shows phase separation at about 40° C. at a storage period of about 24 h.

TABLE 4

| Concentrated Composition obtained by mixing the components | | | |
|---|---|---|---|
| Components | V7 wt.-% | V8 wt.-% | V9 wt.-% |
| $H_2O$ | add. 100 wt.-% | add. 100 wt.-% | add. 100 wt.-% |
| Acetic Acid 80% | 42.25 | 41.75 | 41.25 |
| Octanoic Acid | — | — | — |
| $H_2O_2$ 50% | 41.10 | 40.60 | 40.10 |
| HEDP[*1] | 1.00 | 1.00 | 1.00 |
| Sulfocarboxylic acid[*2] | 3.00 | 4.00 | 5.00 |
| Cumolsulfat | 10.10 | 10.20 | 10.31 |
| Total | 100 wt.-% | 100 wt.-% | 100 wt.-% |

[*1] = 1-Hydroxyethane-(1,1-diphosphonic acid)
[*2] = sulphonated oleic acid, preferably Lankropol OPA available from AkzoNobel Table 4 shows the comparison examples V7 to V9 obtained by mixing the components mentioned in table 3 that shows phase separation at about 23° C. at a storage period of about ≤4 days. The phase separation increases from V7 to V9. Thus, the content of $C_6$ to $C_{22}$-sulfocarboxylic acid[*2] has an effect on phase separation. It can be taken from table 1 that adding octanoic acid works against phase separation.

TABLE 5

| CFU (colony forming unit) of the initial state of germs in log/ml | | | |
|---|---|---|---|
| germs | strain | CFU | LOG Reduction |
| Bacillus atrophaeus | ATCC 9372 | $2.6 \times 10^3$ | 3.79 |
| Bacillus cereus | N1009 | $8.4 \times 10^3$ | 3.51 |

The bactericidal activity of compositions according to the invention was tested under simulated high soiling conditions on soy agar and incubation time of 35° C. for 48 hours. The compositions of E1 to E6 and V1 to V9 were diluted in deionized water with a ratio of 1:50 to obtain a use composition. The experiments were performed according to standard procedures for the following germs: Bacillus atrophaeus and Bacillus cereus. The disinfectant exhibited for E1 to E6 a complete elimination of all tested germs by a factor of at least $10^3$ at testing time of 15 seconds for Bacillus atrophaeus and 20 seconds for Bacillus cereus at a test temperature of 50° C.

Phase separation of the composition of V1 to V9 has the drawback that the bactericidal and fungicidal activity becomes dramatically worse, so that the CFU average reduction factors cannot be suitable determined, about less than 1 log reduction. Moreover, due to the phase separation of said compositions V1 to V9 the contained sulfocarboxylic acid and other components thereof precipitate on the surfaces that were exposed to said compositions. Thus, compositions of V1 to V9 cannot be used in CAF, CIP and COP processes.

Other Embodiments

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims.

In addition, the contents of all patent publications discussed supra are incorporated in their entirety by this reference.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

We claim:

1. A liquid composition comprising a mixture of:
   a) a C6 to C22 sulfoperoxycarboxylic acid,
   b) a $C_1$ to $C_4$ percarboxylic acid,
   c) a $C_5$ to $C_{10}$ percarboxylic acid,
   d) a peroxide agent,
   e) a liquid; wherein the composition comprises free sulfocarboxylic acid, free $C_1$ to $C_4$ carboxylic acid and free $C_5$ to $C_{10}$ carboxylic acid, wherein the weight ratio of C6 to C22 sulfocarboxylic acid to C6 to C22 sulfoperoxycarboxylic acid is about 0.1:1 to about 25:1.

2. The composition of claim 1, wherein the weight ratio of C6 to C22 sulfocarboxylic acid to C6 to C22 sulfoperoxycarboxylic acid is about 5:1 to about 20:1.

3. The composition of claim 1, wherein the sulfoperoxycarboxylic acid is a compound according to Formula I and the sulfocarboxylic acid is a compound according to Formula II:

$R_1$—CH($SO_3^-X^+$)—$R_2$—COOOH     (Formula I)

$R_1$—CH($SO_3^-X^+$)—$R_2$—COOH     (Formula II)

wherein:
$R_1$ is a substituted or unsubstituted $C_m$ alkyl group, for example $CH_3$—$(CH)_7$—C═C—, preferably hydrogen;
$R_2$ is hydrogen, or a substituted or unsubstituted $C_n$ alkyl group, for example —$(CH_2)_6$—, preferably hydrogen;
X is hydrogen, a cationic group, or an ester-forming moiety, preferably hydrogen;
m is 1 to 10, preferably 8 to 10;
n is 1 to 10; preferably 6 to 8; and
m+n is less than or equal to 18, or salts or esters thereof; preferably the sulfoperoxycarboxylic acid is

$CH_3$—$(CH)_7$—C═C—CH($SO_3^-X^+$)—$(CH_2)_6$—COOOH, and the sulfocarboxylic acid is

$CH_3$—$(CH)_7$—C═C—CH($SO_3^-X^+$)—$(CH_2)_6$—COOH.

4. The composition of claim 1, wherein the composition comprises sulfoperoxycarboxylic acids of the formula IIIa to VIIa and/or sulfocarboxylic acids of the formula IIIb to VIIb:

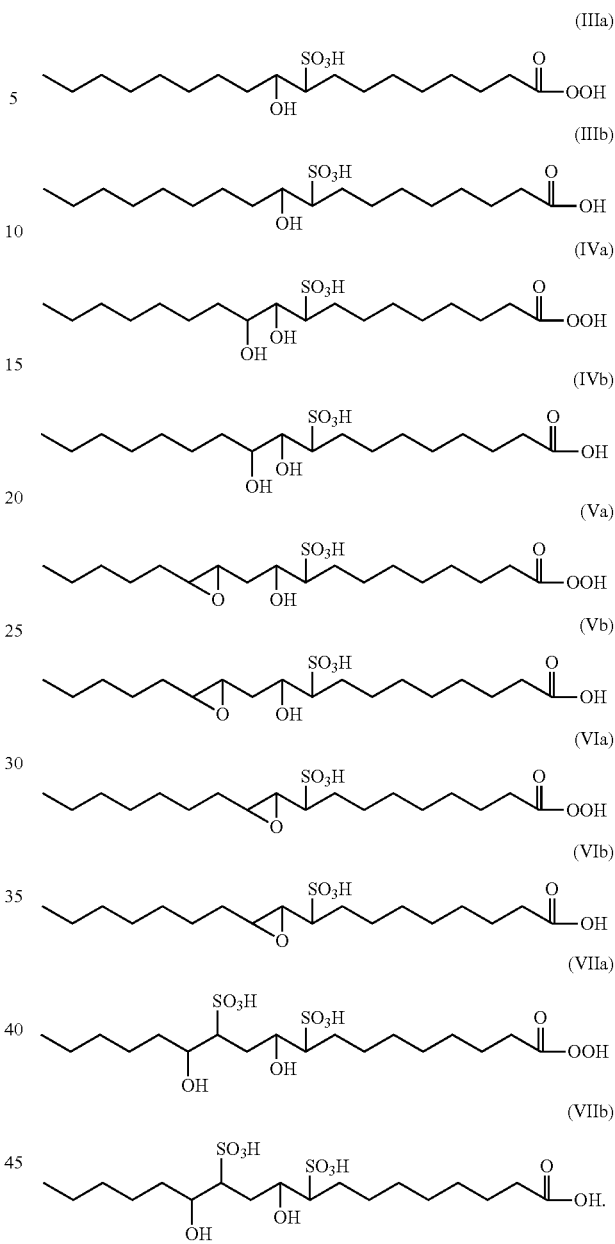

5. The composition of claim 1, wherein the composition comprises at least one chelant, comprising dipicolinic acid, phosphonic acid or salt thereof.

6. The composition of claim 5 wherein the phosphonic acid or salt thereof is selected from the group comprising 2-aminoethylphosphonic acid, dimethyl methylphosphonate, 1-hydroxy ethylidene-1,1-diphosphonic acid, amino tris(methylene phosphonic acid), ethylenediamine tetra(m-ethylene phosphonic acid), tetramethylenediamine tetra(m-ethylene phosphonic acid), hex amethylenediamine tetra (methylene phosphonic acid), diethylenetriamine penta (methylene phosphonic acid), phosphonobutane-tricarboxylic acid, N-(phosphonomethyl)iminodiacetic acid, 2-carboxyethyl phosphonic acid, 2-hydroxyphosphonocarboxylic acid, amino-tris-(methylene-phosphonic acid) and/or salts thereof.

7. The composition of claim 1, wherein the $C_1$ to $C_4$ percarboxylic acid is peroxyacetic acid, the $C_5$ to $C_{10}$ percarboxylic acid is peroxyoctanoic acid, the $C_1$ to $C_4$ carboxylic acid is acetic acid, and/or the $C_5$ to $C_{10}$ carboxylic acid is octanoic acid.

8. The composition of claim 1, wherein the peroxide agent comprises at least one hydrogen peroxide, a perborate, or a percarbonate.

9. The composition of claim 1, wherein the composition comprises at least one hydrotrope selected from the group of an aromatic hydrocarbon sulfonate or aromatic hydrocarbon sulfonic acid.

10. The composition of claim 9 wherein the hydrotrope comprises xylene sulfonate, toluene sulfonate, cumene sulfonate, n-octane sulfonate, and/or acids thereof.

11. The composition of claim 1, wherein the composition is free of an additional acidulant.

12. The composition of claim 1 wherein the composition comprises an acidulant.

13. The composition of claim 12 wherein the additional acidulant is comprised of about >0 wt.-% to about ≤20 wt.-% sulfuric acid, based on the total weight of the concentrated liquid composition.

14. The composition of claim 1, wherein the additional acidulant is selected from the group consisting of sulfuric acid, sodium bisulfate, nitric acid, hydrochloric acid, methane sulfonic acid, ethane sulfonic acid, propane sulfonic acid, butane sulfonic acid, formic acid, acetic acid, halocarboxylic acids, picolinic acid, dipicolinic acid, and mixtures thereof.

15. The composition of claim 1, wherein a concentrated liquid composition comprises:
    about ≥0.001 wt.-% to about ≤2 wt.-% of at least one C6 to C22 sulfoperoxycarboxylic acid comprised of sulphonated peroxyoleic acid;
    about ≥0.01 wt.-% to about ≤25 wt.-% of at least one C6 to C22 sulfocarboxylic acid comprised of sulphonated oleic acid;
    about ≥2.5 wt.-% to about ≤16.5 wt.-% of a C1 to C4 carboxylic acid comprised of acetic acid;
    about >0 wt.-% to about ≤8 wt.-% of at least one C5 to C10 percarboxylic acid comprised of peroxyoctanoic acid;
    about >0 wt.-% to about ≤10 wt.-% of a $C_5$ to $C_{10}$ carboxylic acid comprised of octanoic acid;
    about ≥5 wt.-% to about ≤30 wt.-% of at least one peroxide agent comprised of hydrogen peroxide;
    about ≥0 wt.-% to about ≤20 wt.-% of a hydrotrope, selected from the group comprising xylene sulfonate, toluene sulfonate, or cumene sulfonate, n-octane sulfonate, and/or acids thereof;
    about ≥0 wt.-% to about ≤10 wt.-% of a chelant comprised of 1-hydroxyethane-(1,1-diphosphonic acid) (HEDP);
    about ≥0 wt.-% to about ≤20 wt.-% of at least one acidulant comprising sulfuric acid; and
    a solvent comprised of water, wherein the components are selected such that the total weight amount of all components of the concentrated liquid composition is 100 wt.-%.

16. The composition of claim 1, wherein the composition is obtained by mixing the components:
    i) about ≥10 wt.-% to about ≤30 wt.-% of at least one peroxide agent;
    ii) carboxylic acids of:
        about ≥0.01 wt.-% to about ≤25 wt.-% of at least one C6 to C22 sulfocarboxylic acid,
        about ≥10 wt.-% to about ≤60 of at least one C1 to C4 carboxylic acid,
        about ≥0.01 wt.-% to about ≤10%, of at least one $C_5$ to $C_{10}$ carboxylic acid, preferably octanoic acid;
    iii) about ≥0 wt.-% to about ≤20 wt.-%, of at least one hydrotrope;
    iv) about ≥0 wt.-% to about ≤10 wt.-% of a chelant;
    v) solvent, preferably water, wherein the components are selected such that the total weight amount of all components of the concentrated liquid composition is 100 wt.-%.

17. The composition of claim 1, wherein the concentrated composition is further diluted with a solvent to obtain a use solution.

18. A method for removing soil and/or reducing a population of organism, spore and/or fungi on a surface comprising applying to the surface a composition of claim 1.

19. The method of claim 18, wherein the composition is applied to the surface at between about ≥0° C. to about ≤80° C.

* * * * *